(12) United States Patent
Capote

(10) Patent No.: US 10,695,103 B2
(45) Date of Patent: Jun. 30, 2020

(54) MOTION CONTROL AND VERTEBRAL FIXATION DEVICE

(71) Applicant: Warsaw Orthopedic, Inc, Warsaw, IN (US)

(72) Inventor: Cristian A. Capote, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/940,484

(22) Filed: Mar. 29, 2018

(65) Prior Publication Data

US 2019/0298421 A1 Oct. 3, 2019

(51) Int. Cl.
*A61B 17/70* (2006.01)
*A61B 17/80* (2006.01)
*A61F 2/44* (2006.01)
*A61F 2/46* (2006.01)
*A61B 17/02* (2006.01)

(52) U.S. Cl.
CPC ...... *A61B 17/7044* (2013.01); *A61B 17/7059* (2013.01); *A61B 17/8004* (2013.01); *A61B 17/8023* (2013.01); *A61B 17/8033* (2013.01); *A61F 2/442* (2013.01); *A61F 2/4611* (2013.01); *A61B 17/025* (2013.01); *A61B 2017/0256* (2013.01); *A61F 2/4455* (2013.01); *A61F 2002/448* (2013.01)

(58) Field of Classification Search
CPC . A61B 17/7059; A61B 17/80; A61B 17/8023; A61B 17/8033; A61B 17/8047; A61B 17/809
See application file for complete search history.

(56) References Cited

U.S. PATENT DOCUMENTS

| | | | |
|---|---|---|---|
| 5,904,683 A * | 5/1999 | Pohndorf | A61B 17/7059 606/287 |
| 7,828,849 B2 | 11/2010 | Lim | |
| 8,206,390 B2 | 6/2012 | Lindemann | |
| 8,628,578 B2 | 1/2014 | Miller et al. | |
| 9,283,091 B2 | 3/2016 | Melkent et al. | |
| 9,427,328 B2 | 6/2016 | Drochner et al. | |
| 9,414,936 B2 | 8/2016 | Miller et al. | |
| 9,730,684 B2 | 8/2017 | Beale et al. | |
| 2002/0103487 A1* | 8/2002 | Errico | A61B 17/7032 606/247 |
| 2005/0197712 A1* | 9/2005 | Bigsby | A61F 2/3601 623/23.27 |
| 2007/0055242 A1* | 3/2007 | Bailly | A61B 17/7032 606/266 |
| 2007/0173841 A1* | 7/2007 | Ralph | A61B 17/80 606/86 A |
| 2009/0228046 A1* | 9/2009 | Garamszegi | A61B 17/7052 606/278 |
| 2009/0287257 A1* | 11/2009 | Hagen | A61B 17/7059 606/289 |

(Continued)

*Primary Examiner* — Nicholas J Plionis

(57) ABSTRACT

A vertebral fixation plate assembly for securing adjacent vertebral bodies is provided that is configured to distract or extend along its length, as well as provide multiple degrees of freedom between the fixation points and the vertebral fixation plate in order to accommodate different installation locations, as well as different surgical approaches. Methods of using the vertebral fixation plate assembly are also provided.

18 Claims, 8 Drawing Sheets

(56) References Cited

U.S. PATENT DOCUMENTS

| | | | |
|---|---|---|---|
| 2011/0313472 A1* | 12/2011 | Yap | A61B 17/7064 606/305 |
| 2012/0265203 A1* | 10/2012 | Angelucci | A61B 17/7059 606/70 |
| 2014/0228887 A1* | 8/2014 | Raju | A61B 17/7035 606/257 |
| 2016/0000481 A1* | 1/2016 | Ehmke | A61B 17/8009 606/71 |
| 2016/0120660 A1 | 5/2016 | Melkent et al. | |
| 2017/0049653 A1 | 2/2017 | Lim et al. | |
| 2017/0105844 A1 | 4/2017 | Kuyler et al. | |
| 2018/0028246 A1* | 2/2018 | Kang | A61B 17/8605 |

* cited by examiner

MOTION CONTROL AND VERTEBRAL FIXATION DEVICE

TECHNICAL FIELD

The present disclosure generally relates to medical devices for the treatment of musculoskeletal disorders, and more particularly to a fixation device and methods of use for stabilizing the spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. Fixation of vertebrae is a common approach to treating various types of spinal disorders. In general terms, one or more vertebrae are typically fixed in position relative to one or more other vertebrae. Conventional anterior spinal fixation plates typically include a unitary plate having a pair of bone screw openings at opposite ends. These plates may be adjustable, but are sometimes awkward to use, expensive to manufacture, and have larger profiles. The plates may have complex adjustment mechanisms that make adjustment difficult during surgical procedures.

The present invention seeks to address these and other shortcomings in the existing art.

SUMMARY

In one aspect, the present disclosure provides a vertebral fixation plate assembly comprising a first plate having an inward side and an outward side, the first plate comprising a fixation end and a tongue end extending therefrom, wherein the tongue end comprises an elongated aperture extending between the inward side and the outward side; and a second plate having an inward side and an outward side, the second plate comprising a fixation end and a recessed end extending therefrom, wherein the recessed end comprises a recess adapted to receive the tongue end of the first plate, and wherein the inward side of the recessed plate comprises an inward aperture therethrough and the outward side of the recessed plate comprises an outward aperture therethrough.

In some embodiments, the length of the vertebral fixation plate assembly may be adjusted by translating the tongue end of the first plate within the recess of the recessed end of the second plate. In some embodiments, the elongated aperture comprises a first opening on the inward side and a second opening on the outward side and a face between the first opening and second opening, and wherein the width of the second opening is larger than the width of the first opening.

In some embodiments, the vertebral fixation plate assembly further comprises a set screw, wherein the set screw is disposed within the outward aperture and inward aperture of the second plate and through the elongated aperture of the first plate. In some embodiments, the set screw comprises an angled portion configured to contact the face between the first and second opening, whereby the length of the vertebral fixation plate is fixed.

In some embodiments, at least one of the first plate or second plate is shaped to accommodate a curve of a vertebral body. In some embodiments, both the first plate and the second plate are shaped to accommodate a curve of a vertebral body.

In some embodiment, at least one of the fixation end of the first plate or the fixation end of the second plate comprises a fixation end aperture between the inward side and outward side. In some embodiments, the fixation end aperture comprises a collar disposed within the fixation end aperture.

In some embodiments, the vertebral fixation plate assembly further comprises at least one staple, wherein the staple comprises a base portion comprising at least one prong extending therefrom and a curved outer portion, and wherein the curved outer portion is configured to be received by the collar to secure the staple to the first plate or second plate. In some embodiments, the collar and the curved outer portion of the staple form a ball joint having at least, for example two, or preferably three, degrees of rotational freedom, wherein the at least two, or preferably three, degrees of rotational freedom are selected from roll, pitch, and yaw. In some embodiments, the at least two degrees of rotational freedom are pitch and yaw, and wherein the ball joint provides up to 15° of pitch and up to 15° of yaw. In some embodiments, the curved outer portion of the staple is received by the collar using a snap-fit connection. In some embodiments, the staple comprises a bone screw aperture.

In some embodiments, the vertebral fixation plate assembly further comprises a lock screw configured to be received within the fixation end aperture to secure the position of the staple relative to the fixation end aperture by restricting one or more of the at least two, or preferably three, degrees of rotational freedom.

The present disclosure also provides a vertebral fixation plate assembly, comprising a first plate having an inward side and an outward side, the first plate comprising a fixation end and a tongue end extending therefrom, wherein the tongue end comprises an elongated aperture extending between the inward side and the outward side, and wherein the fixation end of the first plate comprises a first plate fixation end aperture between the inward side and outward side, wherein the first plate fixation end aperture comprises a first collar disposed within the first plate fixation end aperture; a second plate having an inward side and an outward side, the second plate comprising a fixation end and a recessed end extending therefrom, wherein the recessed end comprises a recess adapted to receive the tongue end of the first plate, and wherein the inward side of the recessed plate comprises an inward aperture therethrough and the outward side of the recessed plate comprises an outward aperture therethrough, and wherein the fixation end of the second plate comprises a first plate fixation end aperture between the inward side and outward side, wherein the second plate fixation end aperture comprises a second collar disposed within the second plate fixation end aperture; a first staple, wherein the first staple comprises a base portion comprising at least one prong extending therefrom and a curved outer portion, and wherein the curved outer portion is configured to be received by the first collar to secure the first staple to the first plate; and a first second, wherein the second staple comprises a base portion comprising at least one prong extending therefrom and a curved outer portion, and wherein the curved outer portion is configured to be received by the second collar to secure the second staple to the second plate.

In another aspect, the present disclosure provides a method of installing a vertebral fixation plate assembly, the method comprising providing a first staple, wherein the first staple comprises a base portion comprising at least one prong extending therefrom and a curved outer portion and an aperture through the curved outer portion and the base portion; inserting a first bone screw through the aperture of the first staple to secure the first staple to a first vertebral body; providing a second staple, wherein the second staple comprises a base portion comprising at least one prong extending therefrom and a curved outer portion and an aperture through the curved outer portion and the base portion; inserting a second bone screw through the aperture of the first staple to secure the second staple to a second vertebral body adjacent to the first vertebral body; providing a vertebral fixation plate, the vertebral fixation plate comprising a first plate having an inward side and an outward side, the first plate comprising a fixation end and a tongue end extending therefrom, wherein the tongue end comprises an elongated aperture extending between the inward side and the outward side, and wherein the fixation end of the first plate comprises a first plate fixation end aperture between the inward side and outward side, wherein the first plate fixation end aperture comprises a first collar disposed within the first plate fixation end aperture; and a second plate having an inward side and an outward side, the second plate comprising a fixation end and a recessed end extending therefrom, wherein the recessed end comprises a recess adapted to receive the tongue end of the first plate, and wherein the inward side of the recessed plate comprises an inward aperture therethrough and the outward side of the recessed plate comprises an outward aperture therethrough, wherein the fixation end of the second plate comprises a first plate fixation end aperture between the inward side and outward side, wherein the second plate fixation end aperture comprises a second collar disposed within the second plate fixation end aperture; and engaging the first staple within the first plate fixation end aperture to attach the first plate to the first staple; and engaging the second staple within the second plate fixation end aperture to attach the second plate to the second staple.

In some embodiments, the method further comprises adjusting the lordotic angle between the first and second vertebral bodies, whereby the length of the vertebral fixation plate is changed. In some embodiments, the method further comprises inserting a set screw within the outward aperture and inward aperture of the second plate and through the elongated aperture of the first plate, whereby the length of the vertebral fixation plate is fixed. In some embodiments, the method further comprises inserting a first lock screw into the first plate fixation end aperture, whereby the relative position between the first staple and the first plate is fixed; and inserting a second lock screw into the second plate fixation end aperture, whereby the relative position between the second staple and the second plate is fixed.

BRIEF DESCRIPTION OF THE DRAWINGS

The present disclosure is further informed by the specific description accompanied by the following drawings, in which.

DETAILED DESCRIPTION

Figure 1:
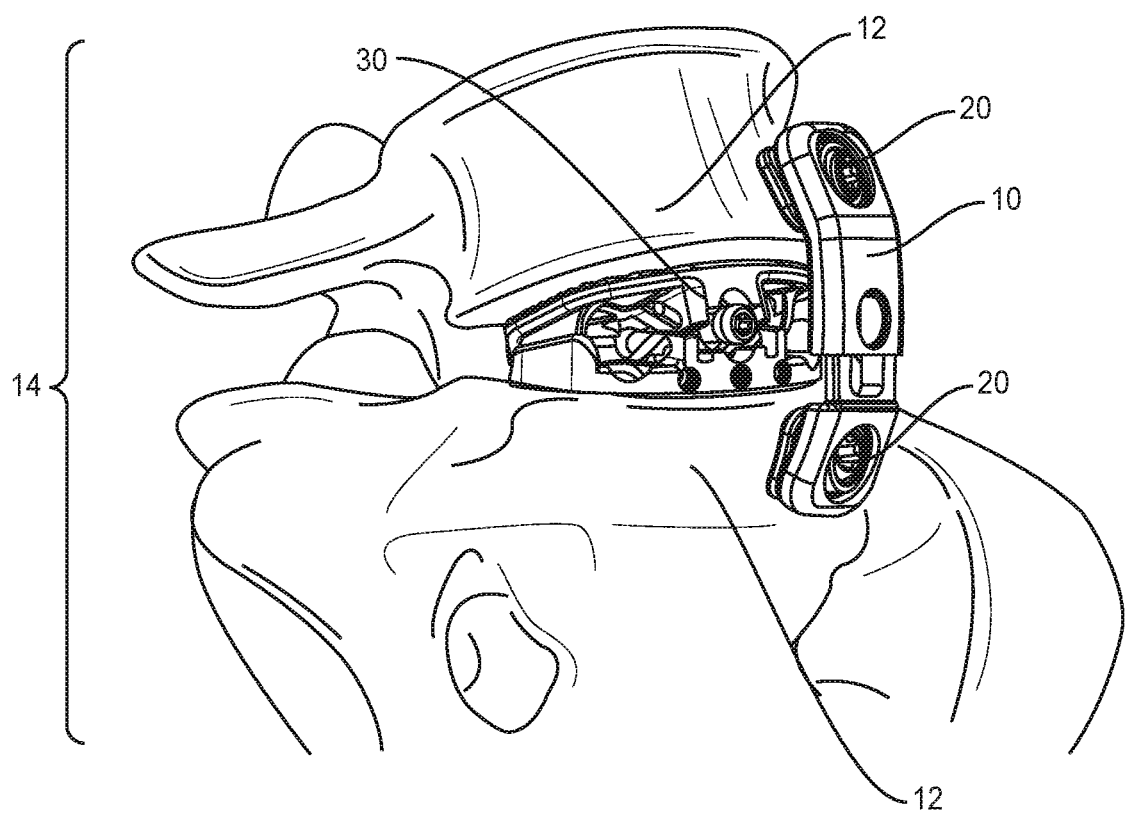
FIG. 1 is a perspective view of a representative vertebral fixation plate assembly in accordance with the principles of the present disclosure.
Figure 2:
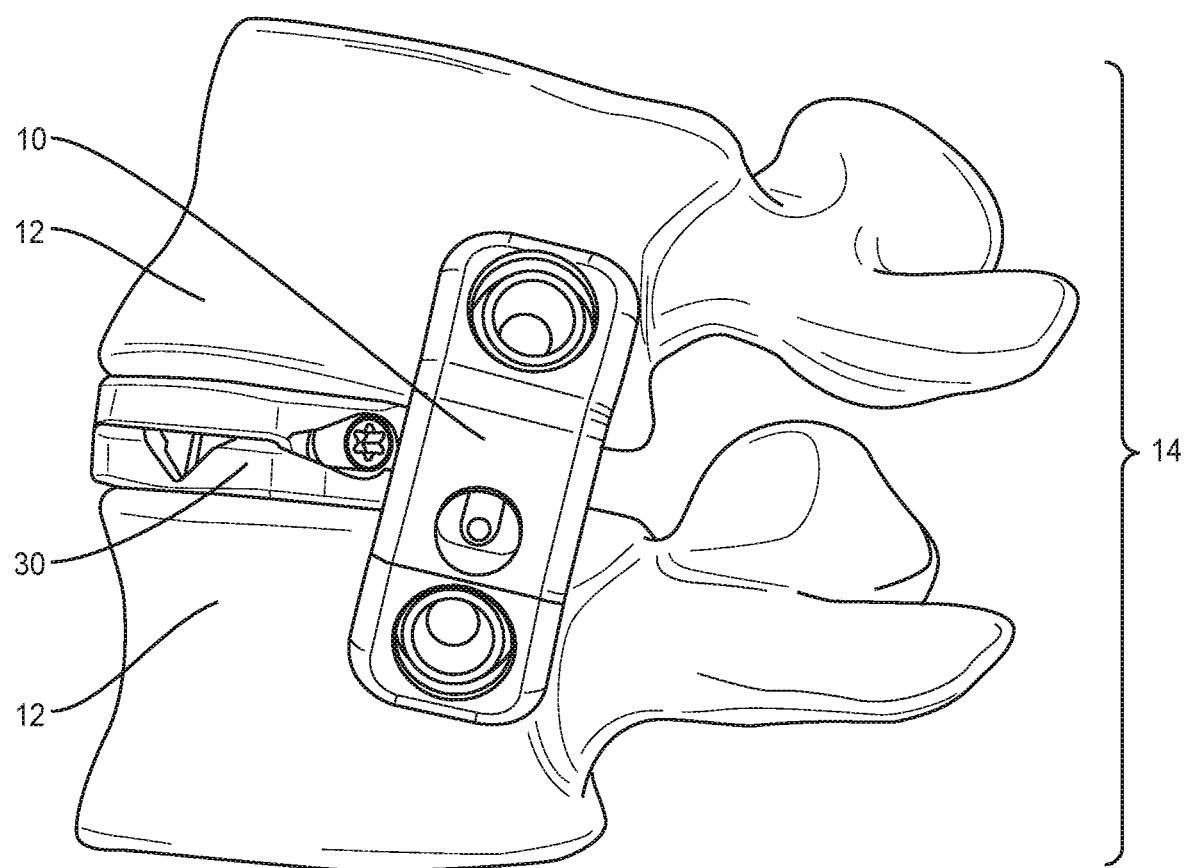
FIG. 2 is a perspective view of a representative vertebral fixation plate assembly in accordance with the principles of the present disclosure.
Figure 3:
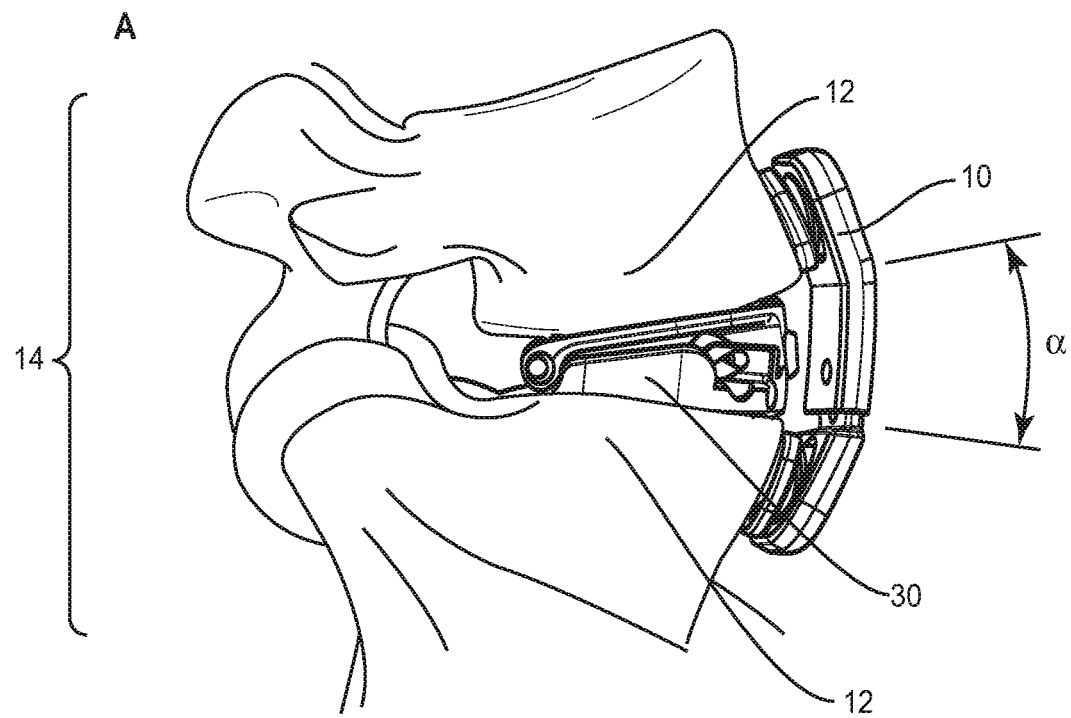
FIG. 3 is a perspective view of a representative vertebral fixation plate assembly installed at (A) a low lordotic angle and (B) a large lordotic angle in accordance with the principles of the present disclosure.
Figure 3:
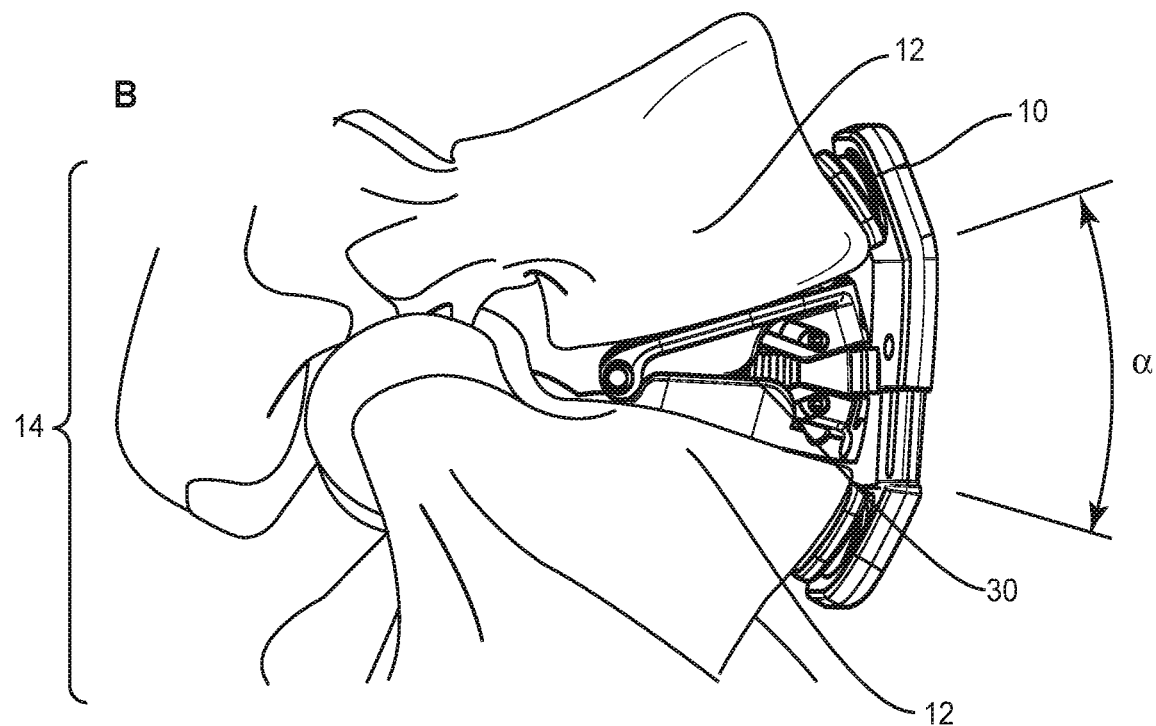
Figure 4:
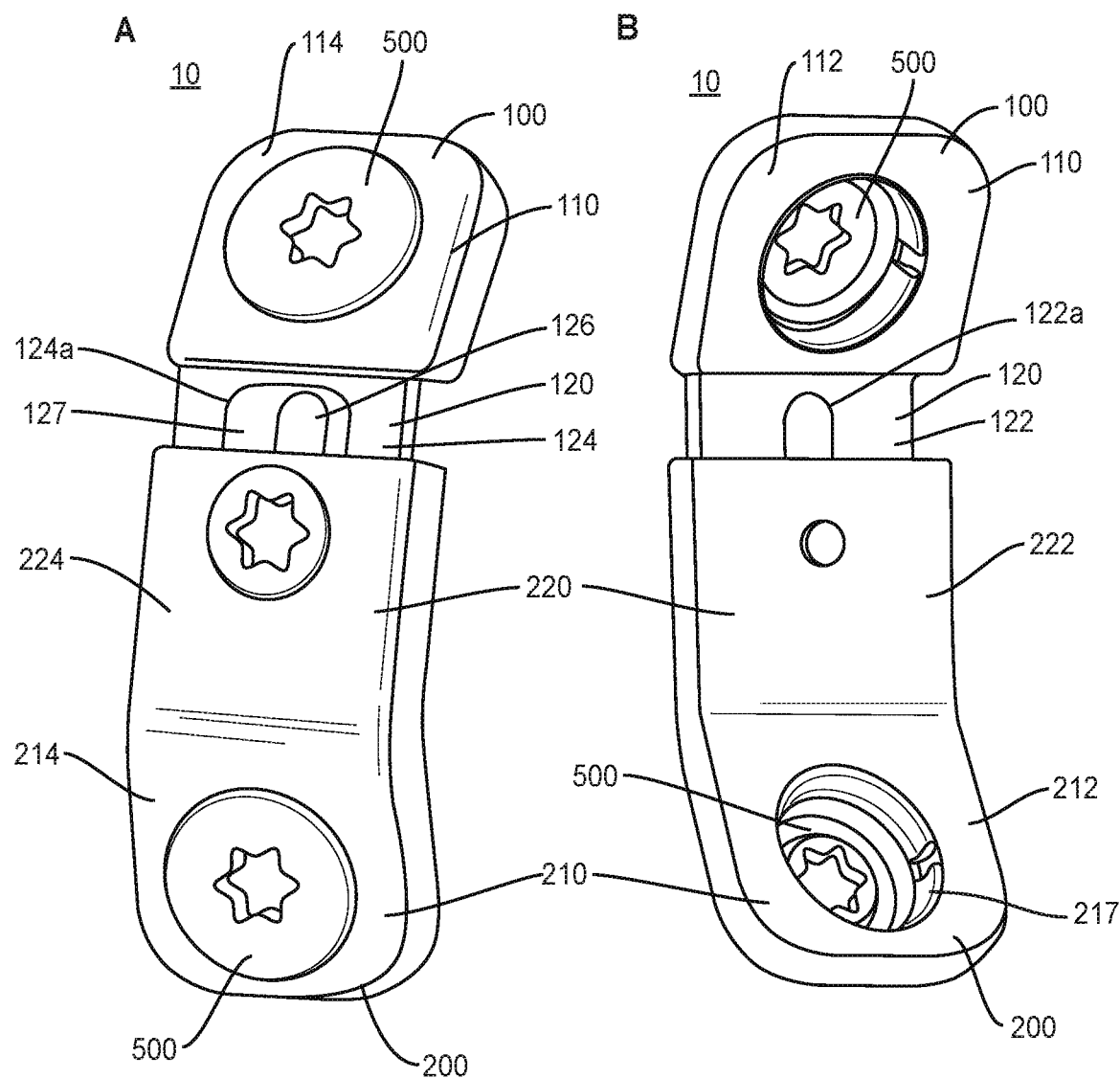
FIG. 4 is a perspective view of the (A) outward side and (B) inward side of a representative vertebral fixation plate in accordance with the principles of the present disclosure.

The exemplary embodiments of the surgical system and related methods of use disclosed are discussed in terms of medical devices for the treatment of musculoskeletal disorders and more particularly, in terms of a vertebral fixation plate for use during various spinal procedures and that may be used in conjunction with other devices and instruments related to spinal treatment, such as spinal implants (e.g., expandable spinal implants), insertion instruments, specialized instruments such as, for example, expandable retractors and spinal surgical tables that rotate and bend the patient in various directions, and/or a method or methods for treating a spine, such as the tables, patient positioning frames, and the like, and related methods of using them include those described in, e.g., U.S. patent application Ser. Nos. 15/239,239, 15/239,256, 15/337,157, 15/638,802, 15/639,080, 15/672,005, and 15/674,456, all incorporated herein by reference in their entirety.

In some embodiments, the present system includes a vertebral bone plate assembly suitable for use in various spinal procedures, in particular a direct lateral interbody fusion (sometimes referred to as DLIF procedures), oblique lateral interbody fusion (sometimes referred to as OLIF procedures), and anterior lumbar interbody fusions (sometimes referred to as ALIF procedures), or variations of these procedures in which the present bone plate assembly is secured to adjacent vertebral bodies to stabilize at least one vertebral level and may further help to secure an intervertebral implant, including, for example, by connecting to the intervertebral implant by pin, screw, or other fixation device or by physically blocking the retropulsion of the intervertebral implant.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following discussion includes a description of a vertebral fixation plate, related components and methods of employing the vertebral fixation plate in accordance with the principles of the present disclosure. Reference is made in detail to the exemplary embodiments of the present disclosure, which are illustrated in the accompanying figures. Turning to FIGS. 1-8 there are illustrated components of a surgical system, such as, for example, a vertebral fixation plate assembly 10.

The components of the vertebral fixation plate described herein can be fabricated from biologically acceptable materials suitable for medical applications, including metals, synthetic polymers, ceramics and bone material and/or their composites. For example, the components of the vertebral fixation plate, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the vertebral fixation plate may be formed or constructed material composites, including the above materials, to achieve various desired characteristics such as strength, rigidity, elasticity, compliance, biomechanical performance, durability and radiolucency or imaging preference. The components of the present vertebral fixation plate, individually or collectively, may also be fabricated from a heterogeneous material such as a combination of two or more of the above-described materials. The components of the vertebral fixation plate may be monolithically formed, integrally connected or include fastening elements and/or instruments, as described herein. The components of the vertebral fixation plate may be formed using a variety of subtractive and additive manufacturing techniques, including, but not limited to machining, milling, extruding, molding, 3D-printing, sintering, coating, vapor deposition, and laser/beam melting. Furthermore, various components of the vertebral fixation plate may be coated or treated with a variety of additives or coatings to improve biocompatibility, bone growth promotion or other features. To the extent the plate is entirely or partially radiolucent, it may further include radiographic markers made, for example of metallic pins, at one or both ends, on each corner of the ends, and/or along the length of the implant in various locations including near the center of the assembly.

The vertebral fixation plate may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the vertebral fixation plate may be employed with surgical procedures, as described herein, and/or, for example, corpectomy, discectomy, fusion and/or fixation treatments that employ spinal implants to restore the mechanical support function of vertebrae. In some embodiments, the expandable spinal implant system may be employed with surgical approaches, including but not limited to: anterior lumbar interbody fusion (ALIF), direct lateral interbody fusion (DLIF), oblique lateral lumbar interbody fusion (OLLIF), oblique lateral interbody fusion (OLIF), various types of anterior fusion procedures, and any fusion procedure in any portion of the spinal column (sacral, lumbar, thoracic, and cervical, for example). The vertebral fixation plate may, in certain embodiments, additionally or alternatively be concave or convexly curved in whole or in part to match or approximate the curvature of the spinal segment or bony location where it is being applied.

Referring now to FIG. 1, a representative vertebral fixation plate assembly 10 is illustrated that is operable to be connected using bone screws 20 to vertebral bodies 12 of a spine 14 to provide alignment and stability. The vertebral fixation plate assembly 10 may be used as an adjunct to fusion of adjacent vertebral bodies 12 or as an adjunct to other surgical procedures performed on the spine 14, or for other general orthopedic uses throughout the body on various bones, including those described above. In the depicted embodiment, the vertebral fixation plate assembly has been installed at an oblique position. Various design aspects, as discussed more fully below, allow a vertebral fixation plate assembly of the present disclosure to be positioned in the lateral plane, anterior plane, or any oblique plane between the two. For example, a vertebral fixation plate assembly of the present disclosure is depicted in a lateral position in FIG. 2. The vertebral fixation plate assembly 10 is being used in conjunction with an expandable spinal implant 30 that may be expanded through a range of angles to provide lordotic or kyphotic correction. Since the spinal implant 30 may provide a range of different lordotic or kyphotic correction angles according the particular needs of a patient during any particular procedure, and further because the size of vertebral bodies 12 and the spacing between vertebral bodies 12 varies from patient to patient, the vertebral fixation plate assembly 10 is operable to be incrementally adjusted to fit various size ranges, as shown in FIGS. 3A and 3B. In FIG. 3A, spinal implant 30 is shown in a closed, collapsed, or partially expanded state, whereas in FIG. 3B, spinal implant 30 has been expanded to provide a larger angle of correction a. Vertebral fixation plate assembly 10 is configured to distract or extend along its length, as well as provide multiple degrees of freedom between the fixation points and vertebral fixation plate 10, in order to accommodate the different orientations required by each scenario. During the operative procedure while the appropriate adjustments to the spine are being made, e.g., increasing the lordotic angle, the vertebral fixation plate assembly restricts the range of distraction and angulation of the spine in the coronal, sagittal and transverse planes so as to ensure no unnecessary trauma occurs.

Referring now to FIGS. 4A and 4B, the vertebral fixation plate assembly 10 includes a first plate 100 and a second plate 200. The second plate 200 is designed to slide over the first plate 100 so as to allow translation of the two plates relative to each other and provide an adjustable length of the vertebral fixation plate 10.

First plate 100 comprises a fixation end 110 and a tongue end 120 that extends therefrom. The fixation end 110 may be substantially planar and have an inward side 112, i.e., the side adjacent the vertebral body, and an outward side 114, i.e., the side away from the vertebral body. In the depicted embodiment, the fixation end is generally square, although the precise shape of fixation end may be varied without substantially interfering with the use of the device. The tongue end 120 is also substantially planar and has an inward side 122 and an outward side 124 and extends from a side of the fixation end. In some embodiments, tongue end 120 may extend at an angle, and/or be curved at least in part, from the fixation end 110 such that the tongue end 120 and fixation end 110 are not co-planar. The angle between the tongue end 120 and fixation end 110 may, for example, be between 0° and 30°, or preferably between 15° and 25°, as measured between the planes of outward sides 114 and 124. The tongue end 120 may be somewhat smaller in width and height than the fixation end 110.

Second plate 200 comprises a fixation end 210 and a recessed end 220 that extends therefrom. The fixation end 210 may be substantially planar, and/or curved at least in part, and have an inward side 212, i.e., the side adjacent the vertebral body, and an outward side 214, i.e., the side away from the vertebral body. In the depicted embodiment, the fixation end is generally square, although the precise shape of fixation end may be varied without substantially interfering with the use of the device. The recessed end 220 is also substantially planar, and/or curved at least in part, and has an inward side 222 and an outward side 224 and extends from a side of the fixation end. In some embodiments, recessed end 220 may extend at an angle from the fixation end 210 such that the recessed end 220 and fixation end 210 are not co-planar. The angle between the recessed end 220 and fixation end 210 may, for example, be between 0° and 30°, or preferably between 15° and 25°, as measured between the planes of outward sides 214 and 224. In some embodiments, the angle between fixation end 210 and recessed end 220 of second plate 200 is substantially the same as the angle between fixation end 110 and tongue end 120 of first plate 100.

Figure 6:
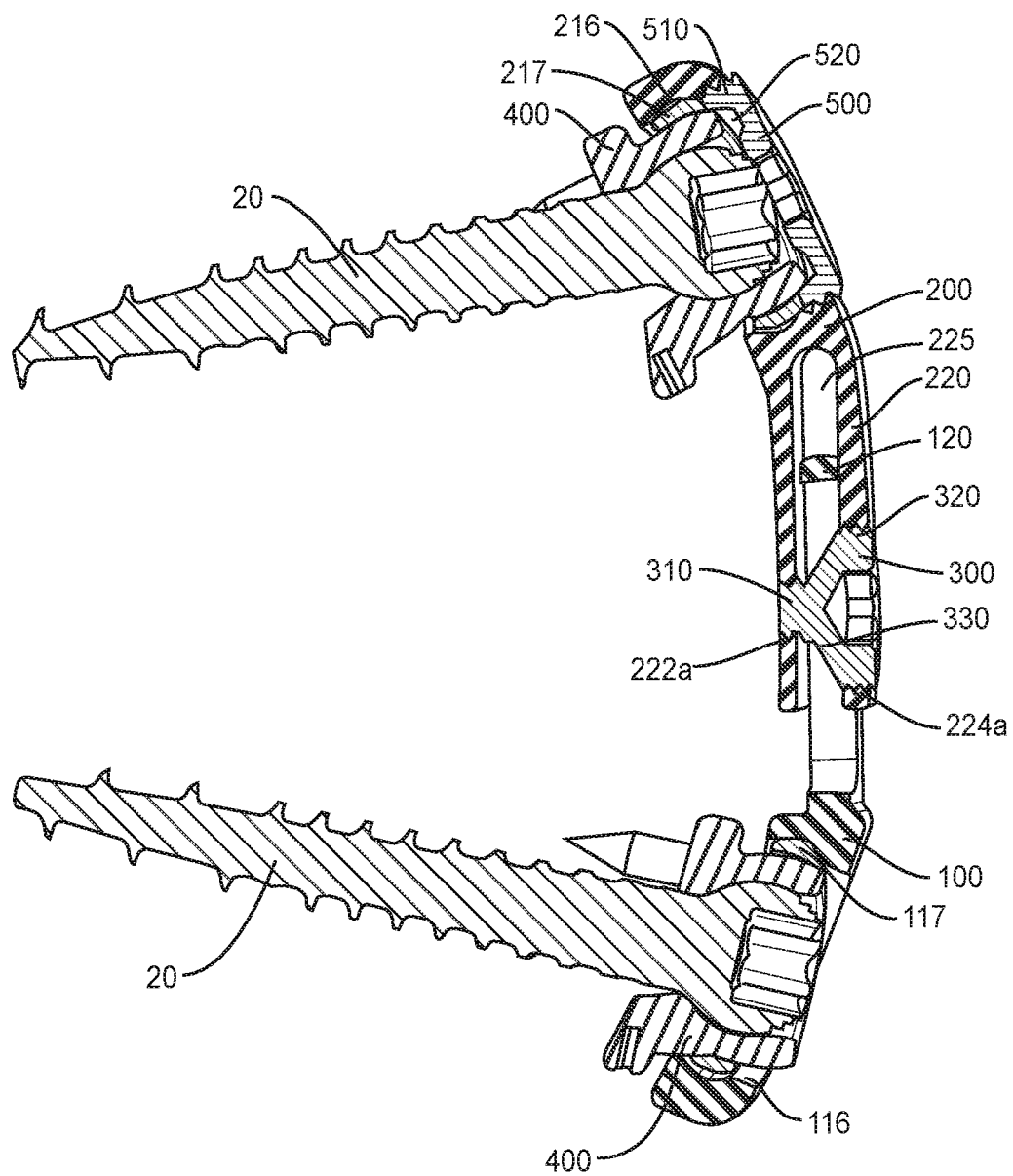
FIG. 6 is a side cut-away view of a representative vertebral fixation plate assembly in accordance with the principles of the present disclosure.

In some embodiments, as shown in FIG. 6, recessed end 220 comprises a recessed portion 225 that is shaped to fit or slide over the tongue end 120 of first plate 100. The outer dimensions of the recessed end 220 may be substantially the same as those of fixation end 210, while the recessed portion is somewhat smaller in width and height and substantially the same size as tongue end 120. The depth of recess 225 is designed to accommodate the full length of tongue end 120 when inserted. First plate 100 and second plate 200 may be distracted, with tongue end 120 translating within recess 225, so as to lengthen and shorten the vertebral fixation plate assembly 10.

When the desired length of the device is achieved, the tongue end 120 and recessed end 220 may be secured via a set screw 300 in order to fix the length of the vertebral fixation plate assembly 10. As shown in FIG. 4A, tongue end 120 may comprise an elongated aperture 126 between inward side 122 and outward side 124 to accommodate set screw 300 along the length of tongue end 120. In some embodiments, the elongated aperture comprises a first opening 122a on the inward side and a second opening on the outward side 124a and a face 127 between the first opening 122a and second opening 124a, and the width of the second opening 124a is larger than the width of the first opening 122a. As can be seen from the figures, face 127 is, for example, oriented at an angle to inward side 122 and outward side 124. In some embodiments, this angle may be 0°, i.e., perpendicular to inward side 122 and outward side 124, to 60°. Recessed end 220 may also comprise a threaded aperture in each of inward side 222 and outward side 224 to accommodate set screw 300. In the depicted embodiment of FIG. 6, the aperture 222a through inward side 222 is smaller than the aperture 224a through outward side 224 so as to accommodate the particular design of the shown set screw 300. Set screw 300 comprises a threaded first end 310 sized so as to engage with the threaded aperture 222a in inward side 222 and a threaded second end 320 sized so as to engage with the threaded aperture 224a in outward side 224. Due to the size differences of first end 310 and second end 320, the middle portion of set screw 300, may, for example, include an angled portion 330. In some embodiments, the angled portion 330 is designed to engage with face 127 of tongue end 120 of first plate 100 and provide a more secure fixation. The engagement between the outer threaded surfaces of set screw 300 and the threaded inner surfaces of apertures 226 and 228 may be via pitch lock, major/minor lock, or any other thread/pitch interface.

Figure 5:
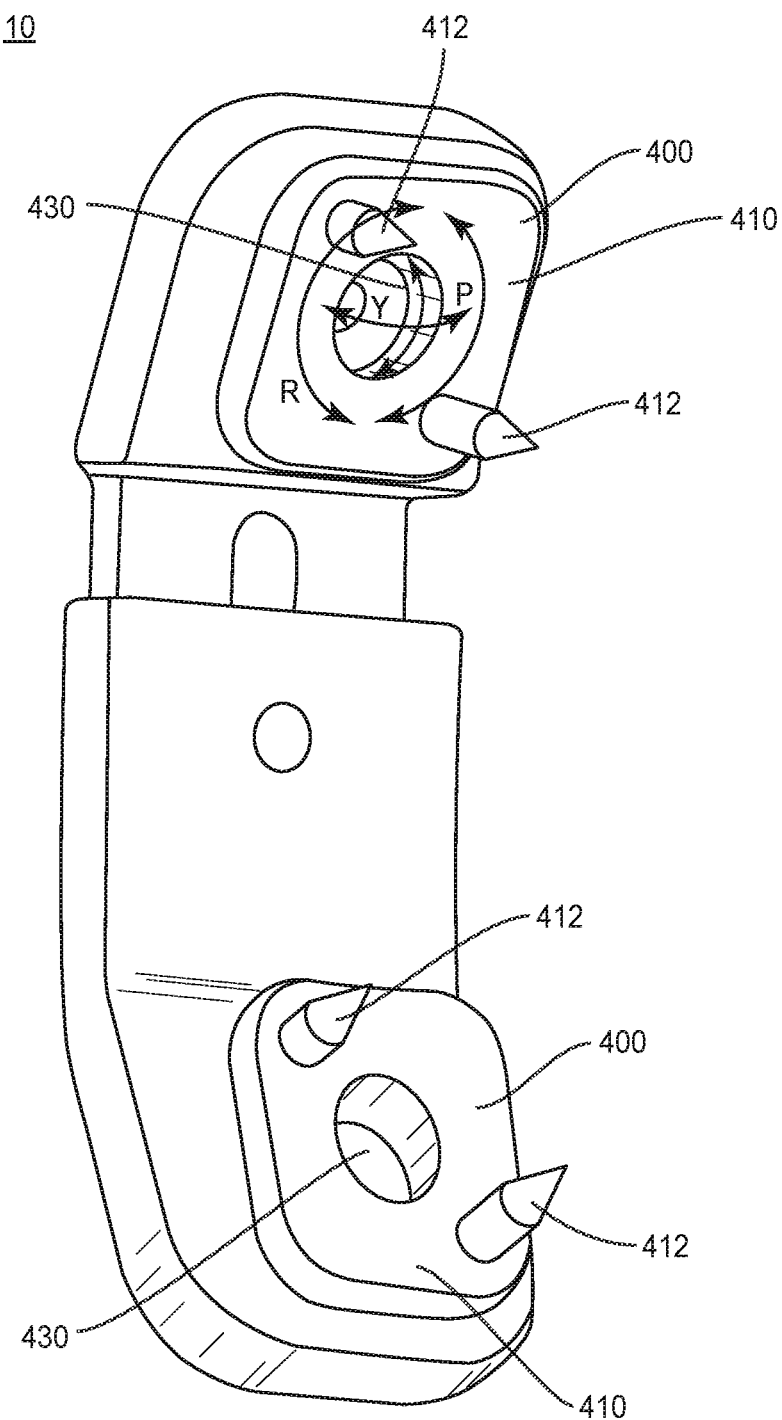
FIG. 5 is a perspective view of the inward side of a representative vertebral fixation plate assembly in accordance with the principles of the present disclosure.
Figure 7:
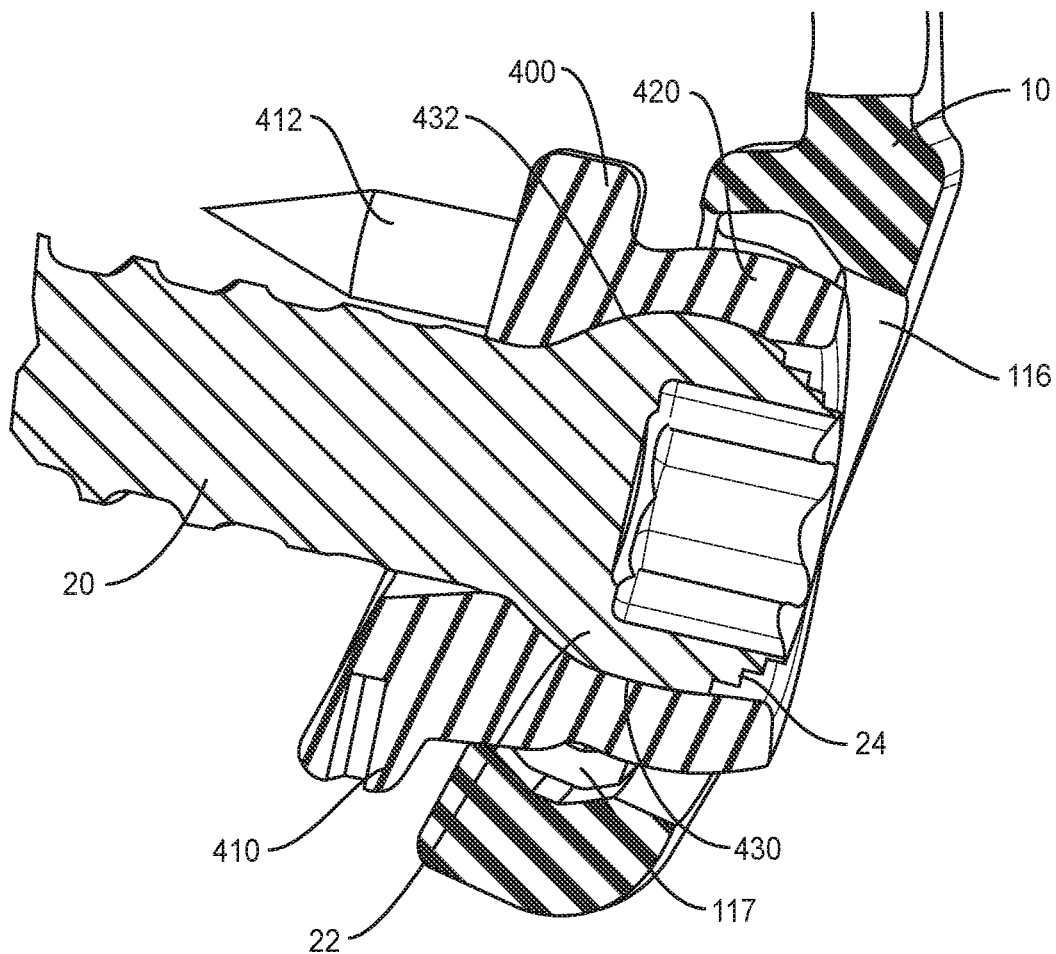
FIG. 7 is a close-up side cut-away view of a representative vertebral fixation plate aperture, staple, and bone screw in accordance with the principles of the present disclosure.
Figure 8:
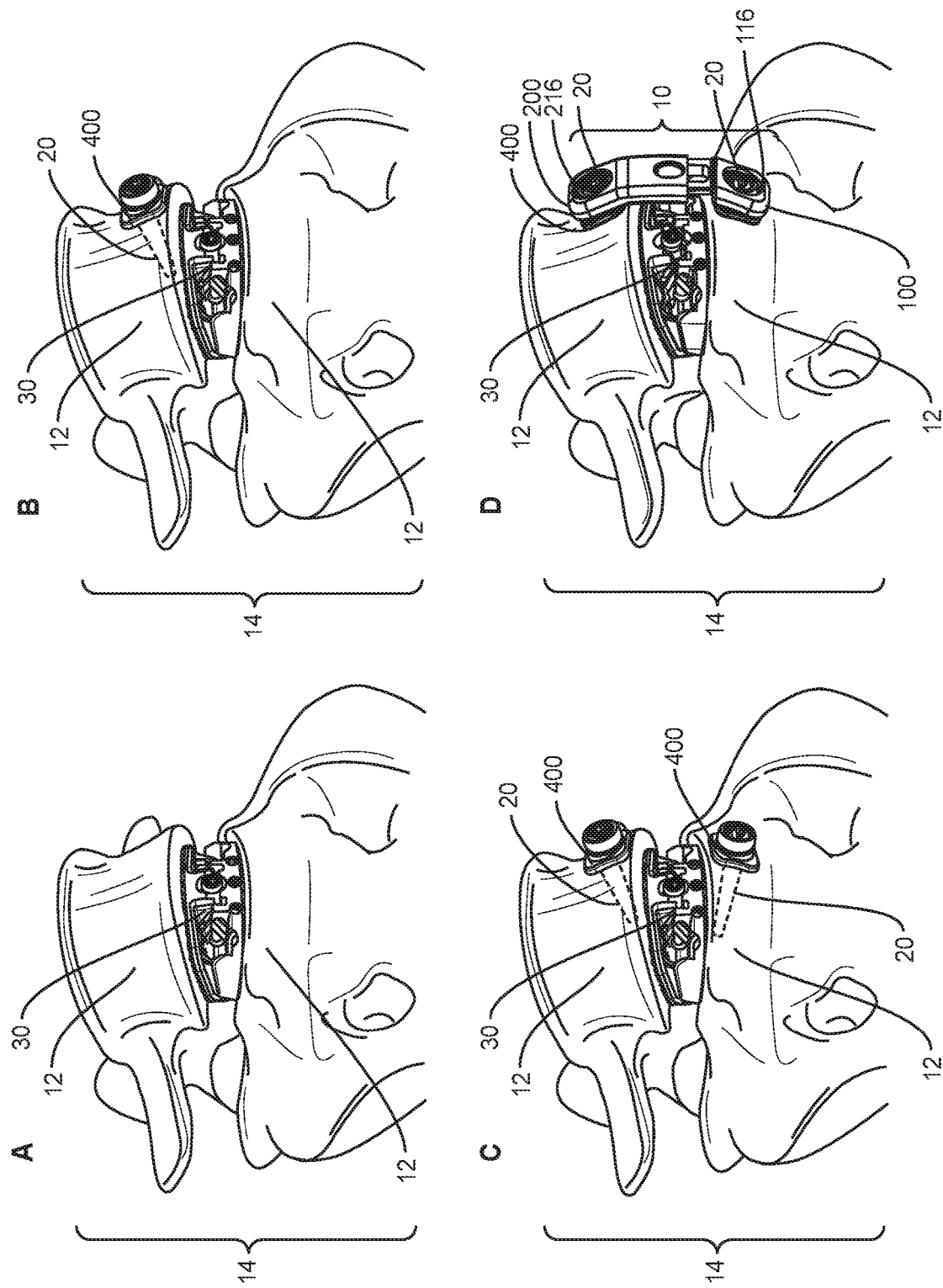
FIG. 8 shows the steps (A)-(D) of a method of installing a vertebral fixation plate assembly in accordance with the principles of the present disclosure

The vertebral fixation plate assembly 10 may be secured to the vertebral bodies 12 with staples 400 and bone screws 20, as depicted in FIG. 7. Staples 400 may comprise a base portion 410 and a curved outer portion 420. Base portion 410 is designed to contact vertebral bodies 12, and may further comprise at least one pin 412 extending therefrom to engage vertebral bodies 12, as shown in FIGS. 5 and 7. Fixation end 110 of first plate 100 may comprise an aperture 116 between the inward side 112 and outward side 114 to hold and receive a staple 400, as shown in FIG. 6. Fixation end 210 of second plate 200 may comprise a similar aperture 216 to hold and receive a staple 400. Staples 400 are configured to fit within apertures 116, 216 and provide, for example, up to at least, for example, two or three degrees of rotational freedom relative to first plate 100 and second plate 200. Curved outer portion 420 of staple 400 is designed to be engaged with a collar 117 within aperture 116, as shown in FIGS. 4B and 7. A similar collar 217 may be disposed within aperture 216, as shown in FIG. 4B. In some embodiments, curved outer portion 420 of staple 400 is secured within apertures 116, 216 via a snap-fit connection. The interaction between curved outer portion 420 and collars 117, 217 functions as a ball joint, allowing the staple 400 to rotate freely, roll, within aperture 116, 216 (as depicted by arrows R in FIG. 5), as well as experience pitch (P) and yaw (Y). In some embodiments, the movement of the staple 400 is, for example, limited to 15 in the pitch and yaw directions. In other embodiments, the staple 400 may, for example, be allowed more freedom of movement, such as 20°, 25°, 30°, or more. The freedom of movement between plates 100, 200 and staples 400 allows the vertebral fixation plate assembly 10 to be used at a variety of different lengths and orientations to the vertebral bodies, i.e., anteriorly, laterally, or obliquely. The orientation between the staple 400 and plate 100 or 200 may be locked using a lock screw 500, as shown in FIGS. 4A, B, and 6. Alternatively, in place of lock screw 500, a cap, cam, wire, spring, adhesive, or locking plate may be incorporated into the plate. Lock screw 500 may comprise a walled portion 510 having external threads and recessed internal portion 520. The external threads of walled portion 510 engage complimentary threading within apertures 116, 216. The curved outer portion 420 of staple 400 fits within the recessed internal portion 520 of walled portion 510 such that walled portion 510 is disposed between staple 400 and the internal wall of apertures 116, 216, thereby securing the ball joint and fixing the relative position of staple 400 and plate 100 or 200.

As shown in FIG. 7, staples 400 may further comprise an aperture 430 therethrough to hold and receive and bone screw 20. The aperture 430 may include a spherical recessed portion 432 that allows a spherical head 22 of a bone screw 20 to be recessed in the apertures 430. The spherical head 22 of bone screw 20 may include one or more ridges or steps 24 for interfacing with the lock screw 500 for a tighter fit. Before the lock screw 500 is tightened the bone screw 20 may be free to move and/or rotate in one or more axis.

Another aspect of the present invention discloses a method for stabilizing at least two adjacent vertebral bodies 12 in a spine 14 using a vertebral fixation plate assembly of the present disclosure. As depicted in FIGS. 8A-D, a spinal implant 30 has been placed within the intervertebral space between two adjacent vertebral bodies 12. Exemplary spinal implants include, e.g., Ser. Nos. U.S. Ser. No. 62/633,952 and U.S. Ser. No. 62/634,033, both incorporated herein by reference in their entirety, and may include other expandable or non-expandable implants, such as, for example, Ser. Nos. U.S. Ser. No. 14/532,636, U.S. Ser. No. 14/885,472, U.S. Ser. No. 14/047,563, U.S. Ser. No. 14/096,769, U.S. Ser. No. 14/203,125, and U.S. Pat. Nos. 8,628,578 and 7,828,849, each incorporated herein in their entirety, implanted unilaterally or bilaterally. In the depicted embodiment, spinal implant 30 is an expandable implant and allows for an adjustment to the desired lordotic angle after insertion into the intervertebral space. The spinal implant may be placed through spinal procedures as known in the art, including anterior lumbar interbody fusion (ALIF), direct lateral interbody fusion (DLIF), oblique lateral lumbar interbody fusion (OLLIF), oblique lateral interbody fusion (OLIF), various types of anterior fusion procedures, and any fusion procedure in any portion of the spinal column (sacral, lumbar, thoracic, and cervical, for example). The staples 400 are then placed into each adjacent vertebral body, as shown in FIGS. 8B and 8C, and secured with bone screws 20. The length of the vertebral fixation plate assembly 10 is adjusted as necessary by distracting first plate 100 from second plate 200. The vertebral fixation plate assembly 10 is then attached by engaging staples 400 within apertures 116, 216, as shown in FIG. 8D. Alternatively, one or both of staples 400 may be pre-installed in the vertebral fixation plate assembly 10 before insertion or attachment to the vertebra. Once in place, additional adjustments can be made to the lordotic angle by, e.g., expanding spinal implant 30 and/or articulating a surgical table, patient positioning frames, and the like, as described in, e.g., U.S. patent application Ser. Nos. 15/239,239, 15/239,256, 15/337,157, 15/638,802, 15/639,080, 15/672,005, and 15/674,456, all incorporated herein by reference in their entirety. As the lordotic angle is adjusted, the range of motion provided by the ball joint interaction of curved outer surface 310 of staples 300 and apertures 116 and 216 allows the vertebral fixation plate assembly 10 to distract or shorten as the length is adjusted. At the same time, the vertebral fixation plate assembly restricts the range of distraction and angulation of the spine in the coronal, sagittal and transverse planes so as to ensure no unnecessary trauma occurs. Once the appropriate lordotic angle is obtained, the length of the vertebral fixation plate assembly 10 may be secured by set screw 300, and the orientation of the the first and second plates relative to the staples may be secured by lock screws 500. In some embodiments, additional vertebral fixation plate assemblies may be used to secure multiple vertebral levels. The set screw 300 may be tightened or loosened at various times during a surgical procedure to provide stability during the procedure as the spine or patient are moved or other portions of the procedure are performed, and to adjust the correction and realignment of the vertebrae.

A medical practitioner obtains access to a surgical site including vertebrae such as through incision and retraction of tissues. Spinal implant systems of the present disclosure can be used in any existing surgical method or technique including open surgery, mini-open surgery, minimally invasive surgery and percutaneous surgical implantation, whereby vertebrae are accessed through a mini-incision, retractor, tube or sleeve that provides a protected passageway to the area, including, for example, an expandable retractor wherein the sleeve is formed from multiple portions that may be moved apart or together and may be inserted with the portions closed or together and then expanded to allow for insertion of implants of larger size than the closed cross section of the unexpanded retractor portions. In one embodiment, the components of the spinal implant system are delivered through a surgical pathway to the surgical site along a surgical approach into intervertebral disc space between vertebrae. Various surgical approaches and pathways may be used. Unilateral approaches such as a transforaminal lumbar interbody fusion (TLIF) approach may also be used to place the implant in a substantially oblique position relative to the vertebrae. Multilateral approaches such as those disclosed in U.S. Pat. No. 9,730,684, incorporated herein by reference in its entirety, may also be used with spinal implant systems of the present disclosure.

As will be appreciated by one of skill in the art, a preparation instrument (not shown) may be employed to remove disc tissue, fluids, adjacent tissues and/or bone, and scrape and/or remove tissue from endplate surfaces of the vertebrae in preparation for the procedures utilizing a system of the present disclosure.

Components of a vertebral fixation plate of the present disclosure can be delivered or implanted as a pre-assembled device or can be assembled in situ. Components of a vertebral fixation plate may be expanded, contracted, completely or partially revised, removed or replaced in situ. In some embodiments, one or all of the components of a vertebral fixation plate of the present disclosure can be delivered to the surgical site via mechanical manipulation and/or a free hand technique.

In one embodiment, additional fastening elements, which may include locking structure, configured for fixation with vertebrae to secure joint surfaces and provide complementary stabilization and immobilization to a vertebral region. In some embodiments, locking structure may include fastening elements, such as, for example, rods, plates, clips, hooks, adhesives, cams, wires and/or flanges. The components of the vertebral fixation plate assembly can be made of radiolucent materials such as polymers. Radiopaque markers may be included for identification under x-ray, fluoroscopy, CT or other imaging techniques. The insertion instrument alone or with the tube for insertion therethrough described above may be radiolucent and may optionally include markers added at the tip and/or along the length of one or both of insertion instrument and the tube to permit them to be seen on fluoroscopy/x-ray while advancing into the patient. The vertebral fixation plate, if radiolucent in whole or part, may also include one or more markers on each end, or in each corner, and/or in various locations along the length of the plate to permit visualization on X-ray or fluoroscopy or by other imaging devices.

In some embodiments, the use of microsurgical, minimally-invasive and image guided technologies may be employed to access, view and repair spinal deterioration or damage, with the aid of spinal implant system. Upon completion of the procedure, the non-implanted components, surgical instruments and assemblies of spinal implant system may be removed and the incision is closed. In some embodiments, the various instruments disclosed may be provided with fiducial markers or other elements suitable for use with surgical navigation systems (including, but not limited to the STEALTHSTATION® Navigation system available from Medtronic).

It will be understood that various modifications may be made to the embodiments disclosed herein. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. The vertebral fixation plate assembly for attachment to a first vertebral body and a second vertebral body, comprising:
    a first plate having an inward side and an outward side, the first plate comprising a fixation end and a tongue end extending therefrom and a first end aperture, wherein the tongue end comprises an elongated aperture extending between the inward side and the outward side;
    a second plate having an inward side and an outward side, the second plate comprising a fixation end and a recessed end extending therefrom and a second end aperture, wherein the recessed end comprises a recess adapted to receive the tongue end of the first plate, and wherein the inward side of the second plate comprises a threaded inward aperture therethrough and the outward side of the second plate comprises a threaded outward aperture therethrough, and wherein the at least one of the first end aperture and the second end aperture comprises a collar disposed therein; and
    a set screw, the set screw comprising a threaded first end configured to engage with the threaded inward aperture of the second plate, a threaded second end configured to engage with the threaded outward aperture of the second plate, and a middle portion configured to pass through the elongated aperture of the tongue end of the first plate;
    at least one bone screw adapted to be received by at least one of the first end aperture and the second end aperture;
    at least one staple, wherein the staple comprises a base portion comprising at least one prong extending therefrom and a curved outer portion, and wherein the curved outer portion is configured to be received by the collar to secure the staple to the first plate or second plate;
    at least one lock screw adapted to selectively fix against movement of the bone screw with respect to the at least one of the first end aperture and the second end aperture, wherein the lock screw comprises external threads and an external wall portion adapted to be disposed between the staple and the at least one of the first end aperture and the second end aperture; and
    the at least one of the first end aperture and the second end aperture comprising threads adapted to threadingly receive the external threads of the lock screw.

2. The vertebral fixation plate assembly of claim 1, wherein the length of the vertebral fixation plate assembly may be adjusted by translating the tongue end of the first plate within the recess of the recessed end of the second plate.

3. The vertebral fixation plate assembly of claim 1, wherein the elongated aperture comprises a first opening on the inward side and a second opening on the outward side and a face between the first opening and second opening, and wherein the width of the second opening is larger than the width of the first opening.

4. The vertebral fixation plate assembly of claim 3, wherein the middle portion of the set screw comprises an angled portion configured to contact the face between the first and second opening, whereby the length of the vertebral fixation plate is fixed.

5. The vertebral fixation plate assembly of claim 1, wherein at least one of the first plate or second plate is shaped to accommodate a curve of a vertebral body.

6. The vertebral fixation plate assembly of claim 5, the first plate and the second plate are shaped to accommodate a curve of a vertebral body.

7. The vertebral fixation plate assembly of claim 1, wherein the collar and the curved outer portion of the staple form a ball joint having at least two degrees of rotational freedom, wherein the at least two degrees of rotational freedom are selected from roll, pitch, and yaw.

8. The vertebral fixation plate assembly of claim 7, wherein the at least two degrees of rotational freedom are pitch and yaw, and wherein the ball joint provides up to 15° of pitch and up to 15° of yaw.

9. The vertebral fixation plate assembly of claim 1, wherein the curved outer portion of the staple is received by the collar using a snap-fit connection.

10. The vertebral fixation plate assembly of claim 7, further comprising the lock screw being configured to secure the position of the staple relative to the at least one of the first end aperture and the second end aperture by restricting one or more of the at least two degrees of rotational freedom.

11. A vertebral fixation plate assembly for attachment to a first vertebral body and a second vertebral body, comprising:
- a first plate having an inward side and an outward side, the first plate comprising a fixation end and a tongue end extending therefrom, wherein the tongue end comprises an elongated aperture extending between the inward side and the outward side, and wherein the fixation end of the first plate comprises a first plate fixation end aperture between the inward side and outward side, wherein the first plate fixation end aperture comprises a first collar disposed within the first plate fixation end aperture;
- a second plate having an inward side and an outward side, the second plate comprising a fixation end and a recessed end extending therefrom, wherein the recessed end comprises a recess adapted to receive the tongue end of the first plate, and wherein the inward side of the second plate comprises an inward aperture therethrough and the outward side of the second plate comprises an outward aperture therethrough, and wherein the fixation end of the second plate comprises a second plate fixation end aperture between the inward side and outward side, wherein the second plate fixation end aperture comprises a second collar disposed within the second plate fixation end aperture;
- a first bone screw having a spherical head;
- a second bone screw having a spherical head;
- a first staple, wherein the first staple comprises a base portion comprising at least one prong extending therefrom, a curved outer portion, and a first staple aperture therethrough comprising a spherical recessed portion adapted to receive the spherical head of the first bone screw, and wherein the curved outer portion is configured to be received in a snap-fit arrangement by the first collar to secure the first staple to the first plate, wherein the first collar and the curved outer portion of the first staple form a first ball joint;
- a second staple, wherein the second staple comprises a base portion comprising at least one prong extending therefrom, a curved outer portion, and a second staple aperture therethrough comprising a spherical recessed portion adapted to receive the spherical head of the second bone screw, and wherein the curved outer portion is configured to be received in a snap-fit arrangement by the second collar to secure the second staple to the second plate, wherein the second collar and the curved outer portion of the second staple form a second ball joint, each of the first ball joint and the second ball joint has at least two degrees of rotational freedom, and the at least two degrees of rotational freedom are selected from roll, pitch, and yaw;
- a first lock screw configured to be received within the first plate fixation end aperture to secure the position of the first staple relative to the first plate fixation end aperture by restricting one or more of the at least two degrees of rotational freedom of the first ball joint, the first lock screw comprising an external wall portion adapted to be disposed between the first staple and the first plate fixation end aperture; and
- a second lock screw configured to be received within the second plate fixation end aperture to secure the position of the second staple relative to the second plate fixation end aperture by restricting one or more the at least two degrees of rotational freedom of the second ball joint, the second lock screw comprising an external wall portion adapted to be disposed between the second staple and the second plate fixation end aperture.

12. The vertebral fixation plate assembly of claim 11, further comprising:
- at least one of the first lock screw and the second lock screw having external threads; and
- at least one of the first plate fixation end aperture and the second plate fixation end aperture being threaded and adapted to threadingly receive the external threads of the at least one of the first lock screw and the second lock screw.

13. The vertebral fixation plate assembly of claim 11, further comprising:
- at least one of the first lock screw and the second lock screw defining a recessed internal portion adapted to receive the curved outer portion of at least one of the first staple and the second staple.

14. A vertebral fixation plate assembly for attachment to a first vertebral body and a second vertebral body, comprising:
- a first plate having an inward side and an outward side, the first plate comprising a fixation end and a tongue end extending therefrom and a first end aperture, wherein the tongue end comprises an elongated aperture extending between the inward side and the outward side;
- a second plate having an inward side and an outward side, the second plate comprising a fixation end and a recessed end extending therefrom and a second end aperture, wherein the recessed end comprises a recess adapted to receive the tongue end of the first plate, and wherein the inward side of the second plate comprises a threaded inward aperture therethrough and the outward side of the second plate comprises a threaded outward aperture therethrough; and
- a set screw, the set screw comprising a threaded first end configured to engage with the threaded inward aperture of the second plate, a threaded second end configured to engage with the threaded outward aperture of the second plate, and a middle portion configured to pass through the elongated aperture of the tongue end of the first plate;
- at least one of the first end aperture and the second end aperture comprising a collar disposed therein;
- at least one staple comprising a base portion having at least one prong extending therefrom and a curved outer portion, and wherein the curved outer portion is received within the collar to secure the staple to the first plate or second plate, and wherein the collar and the curved outer portion form a ball joint having at least two degrees of rotational freedom selected from roll, pitch, and yaw, and wherein the ball joint provides up to 15° of pitch and up to 15° of yaw; and
- at least one lock screw configured to be received within the at least one of the first end aperture and the second end aperture to secure the position of the staple relative to the at least one of the first end aperture and the second end aperture by restricting one or more of the at least two degrees of rotational freedom and comprising an external wall portion adapted to be disposed between the staple and the at least one of the first end aperture and the second end aperture.

15. The vertebral fixation plate assembly of claim 14, further comprising:
- the staple comprising a bone screw aperture; and
- at least one bone screw having a spherical head adapted to be received by the bone screw aperture.

16. The vertebral fixation plate assembly of claim 15, further comprising:

the spherical head of the bone screw having at least one ridge adapted for interfacing with the at least one lock screw.

17. The vertebral fixation plate assembly of claim 14, further comprising:

the at least one lock screw defining external threads; and
at least one of the first end aperture and the second end aperture being threaded and adapted to threadingly receive the external threads of the at least one lock screw.

18. The vertebral fixation plate assembly of claim 14, further comprising:

the at least one lock screw defining a recessed internal portion adapted to receive the curved outer portion of the at least one staple.

* * * * *